US012693284B2

(12) United States Patent
Al-Taq et al.

(10) Patent No.: US 12,693,284 B2
(45) Date of Patent: Jul. 28, 2026

(54) DETERMINING ZETA POTENTIAL OF A CORE SAMPLE

(71) Applicant: Saudi Arabian Oil Company, Dhahran (SA)

(72) Inventors: Ali Abdullah Al-Taq, Qatif (SA); Abdullah Abbas Alrustum, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 131 days.

(21) Appl. No.: 18/435,025

(22) Filed: Feb. 7, 2024

(65) Prior Publication Data

US 2025/0251383 A1 Aug. 7, 2025

(51) Int. Cl.
*G01N 33/24* (2006.01)
*G01N 27/27* (2006.01)

(52) U.S. Cl.
CPC ............ *G01N 33/24* (2013.01); *G01N 27/27* (2013.01)

(58) Field of Classification Search
CPC ................................ G01N 33/24; G01N 27/27
See application file for complete search history.

(56) References Cited

U.S. PATENT DOCUMENTS

| | | | | |
|---|---|---|---|---|
| 3,052,265 | A | * | 9/1962 | Nevill ..................... F16L 55/132 |
| | | | | 138/97 |
| 9,778,226 | B2 | | 10/2017 | Ahmad et al. |

| | | | |
|---|---|---|---|
| 10,167,719 | B2 | 1/2019 | Ezzat et al. |
| 11,458,419 | B2 | 10/2022 | Almubarak et al. |
| 11,542,812 | B2 | 1/2023 | Alghamdi et al. |
| 11,585,742 | B2 | 2/2023 | Al-Boghail et al. |
| 11,852,572 | B2 | 12/2023 | Al-Boghail et al. |

FOREIGN PATENT DOCUMENTS

| | | | | |
|---|---|---|---|---|
| JP | H0772135 | A | * | 3/1995 ............. G01N 27/49 |

OTHER PUBLICATIONS

Glover et al., "Streaming-potential of reservoir rock: A theoretical model," Geophysics, Mar.-Apr. 2012, 77(2):D17-D43, 27 pages.

(Continued)

*Primary Examiner* — Feba Pothen
(74) *Attorney, Agent, or Firm* — Fish & Richardson P.C.

(57) ABSTRACT

A system and a method for determining a zeta potential of a core plug. The system has a first fluid and a second fluid that is less conductive than and immiscible with the first fluid. A core holder holds the core plug. An upstream reservoir, an upstream trap, and an upstream external electrode cell are fluidly coupled to each other and one end of the core holder. A downstream reservoir, a downstream trap, and a downstream external electrode are fluidly coupled to each other and another end of the core holder. A controller determines the zeta potential of the core plug based on the core plug differential pressure and voltage. Each of the upstream reservoir, the downstream reservoir, the upstream trap, and the downstream trap contain some of the second fluid. The first fluid fills the core holder and separates the second fluid from the core holder.

20 Claims, 5 Drawing Sheets

(56) References Cited

OTHER PUBLICATIONS

Jackson et al., "Impact of wettability on laboratory measurements of streaming potential in carbonates," Colloids and Surfaces A: Physicochem. Eng. Aspects, Nov. 2011, 393:86-95, 10 pages.

Luong et al., "Examination of a Theoretical Model of Streaming Potential Coupling Coefficient," International Journal of Geophysics, May 2014, 2014:471819, 12 pages.

Silva et al., "How to account for the concentration dependency of relative permittivity in the Debye-Hückel and Born equations," Fluid Phase Equilibria, Nov. 2022, 566:113671, 16 pages.

* cited by examiner

Streaming Potential for Indiana Limestone (K = 206 md) with 20 mM NaCl in DIW (Reverse 1st)

$y = -0.258x + 2.932$
$R^2 = 0.999$

Cv = -0.258 mv/psi
Cv = -3.741 mv/bar
Cv = -3,741 mv/Mbar

Nacl = 20 mM
Fluid resistivity after coreflood = 4.97 @ 72°F
Saturated core resistivity = 14.620 Kohm Streaming Potential, mV Pressure Drop Across the Core, psi Streaming Potential for Indiana Limestone (K = 206 md) with
20 mM NaCl in DIW (Reverse 3rd)

Streaming Potential for Indiana Limestone (K = 206 md) with
20 mM NaCl in DIW (Reverse 3rd)

DETERMINING ZETA POTENTIAL OF A CORE SAMPLE

TECHNICAL FIELD

This disclosure relates to determining the properties of a core sample, for example, electrical properties such as the zeta potential using a core testing system.

BACKGROUND

Hydrocarbons, other fluids, and particles can be trapped in geologic reservoirs in subterranean formations of the Earth. Samples of the subterranean formation (the rocks and fluids contained within the subterranean formation) can be removed from the Earth during a coring operation. The samples of rock are referred to as a core sample or core plug. The core plug is analyzed to determine the mechanical, fluid, and electrical properties of the rocks and fluids contained within the core sample. The properties of the core plug can be used to design and optimize drilling and completion operations.

One electrical property associated with fluid flow through the subterranean formation is the zeta potential. When fluids with particles flow across a surface of the subterranean formation, a stationary inner layer forms and a moving outer layer of the fluids and particles forms next to the stationary inner layer. The stationary inner layer forms due to relatively stronger electrical bonds with the surface. The moving outer layer flows past the stationary inner layer and has relatively weaker electrical bonds. The difference in electrical charge (a voltage) between the stationary inner layer and the moving outer layer can be measured. This difference in electrical charge between the stationary inner layer and the moving outer layer is the zeta potential. Some core testing systems can have sources of noise and interference which can result in inaccurate testing results.

SUMMARY

This disclosure describes technologies related to determining properties of a core plug using a core testing system. The core testing system determines electrical properties of the core plug such as the zeta potential.

The core testing system of the present disclosure includes a core holder for containing the core sample, a set of upstream components fluidly coupled to one end (the upstream end) of the core holder, another set of downstream components coupled to another end (the downstream end) of the core holder, and instruments to determine the properties of the core sample. The upstream and downstream components electrically isolate the core holder from the other components of the system to reduce sources of noise and interference. The upstream and downstream components include a reservoir, a trap, and an external electrode cell. The upstream and downstream components are filled with two different fluids, with one fluid being less conductive than the other. The two fluids are immiscible, that is, they do not mix with each other. The more conductive fluid is in contact with the core holder, and the less conductive fluid further electrically isolates the core holder from the rest of the core testing system.

Implementations of the present disclosure can realize one or more of the following advantages. For example, this approach can improve the accuracy of core testing. For example, smaller voltages and smaller changes in voltages can be detected because sources of electrical interference and noise from the core testing systems have been reduced by using an insulating fluid, reservoirs, traps, and external electrode cells upstream and downstream of the core holder. By increasing the accuracy of core testing, completion operations such as oil recovery can be improved to optimize oil production from the subterranean formations.

This approach can also improve core testing results. For example, sources of noise and interference can be reduced, improving core testing results.

The details of one or more implementations of the subject matter described in this disclosure are set forth in the accompanying drawings and the description below. Other features, aspects, and advantages of the subject matter will become apparent from the description, the drawings, and the claims.

DETAILED DESCRIPTION

The present disclosure describes systems and methods for determining properties of core samples. Specifically, by measuring the streaming potential (e.g., voltages across the core sample measured while flowing fluid through the core sample), electrical properties such as specific charge and zeta potential at different testing conditions can be determined. The relationship between the streaming potential and the surface electrical charge and between the surface electrical charge and wettability allow streaming potential to be used to assess the change in-situ in the wetting state of the mineral surface of intact carbonate core samples. Accurate measurements of the zeta potential can be used to improve design of completion operations to improve oil recovery and increase production from subterranean formations, especially for operations such as salinity waterflooding or water injection. When the system electrical noise contributes significantly to the measured streaming potential signal, it can yield results which are not presentive results of actual streaming potential generated by the downhole water flow through formation rock and thus its utilization to improve oil recovery and increase production may not be realized.

The fluids in the subterranean formations can include water, hydrocarbon oils and gases, chemicals, and minerals. Some of the hydrocarbons, chemicals, and minerals can be particles. The fluids and particles can exist as a colloidal solution. Colloidal solutions (colloids) are mixtures of fluids and particles where the particles are dispersed and suspended throughout the fluid.

As the colloidal solution (fluids and particles in the reservoir) move through the subterranean formation, some of the fluid electrically couples to the rock and forms a stationary fluid layer. The remainder of the fluid continues to flow. The difference between the stationary fluid layer and the flowing fluids is the zeta potential.

A sample of the subterranean formation can be removed by a coring operation and tested to determine the properties of the subterranean formation, such as the zeta potential. The sample of the subterranean formation can be referred to as a core sample or a core plug. The core plug can be tested using a core testing system. In some cases, the zeta potential is very small, on the order of zero to twenty millivolts (mV).

Figure 1:
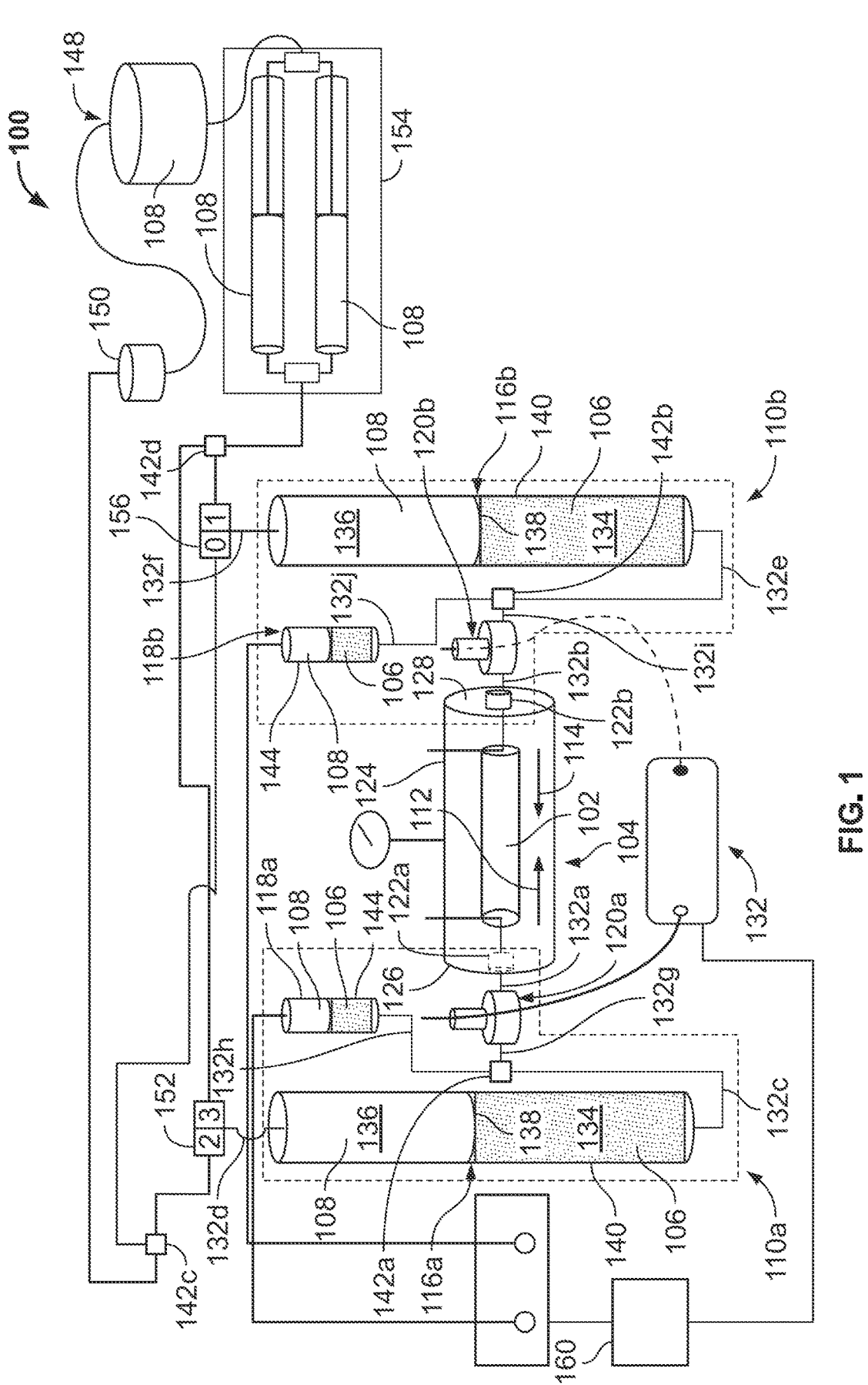
FIG. 1 is a schematic view of a core testing system.

FIG. 1 is a schematic view of a core testing system 100. The core testing system 100 electrically isolates a core plug 102 to reduce electrical interference and noise from other components of the system to more accurately determine the zeta potential of the core plug 102. The core testing system 100 includes a core holder 104 holding the core plug 102. The core testing system 100 is filled with a first fluid 106 and a second fluid 108 that do not mix. The first fluid 106 flows through the core holder 104 to test the core plug 102. The second fluid 108 and two sets 110a, 110b of components (described in more detail below) electrically isolate the core plug 102 to improve the detectability of low voltages.

The first fluid 106 is a testing fluid which is flowed through the core holder 104 containing the core plug 102 to generate the steaming potential. The first fluid 106 is a conductive fluid with particulates. The first fluid 106 can be representative of a production fluid, for example, a fluid used in salinity waterflooding operations. In this implementation, the first fluid 106 is brine. In this implementation, the brine has a permittivity of between 70 and 90, however any acceptable permittivity may be used.

The permittivity can be calculated as a function of salt concentration and temperature using the correlation:

$$\varepsilon_r(T, C_f) = a_0 + a_1 T + a_2 T^2 + a_3 T^3 + c_1 C_f + c_2 C_f^2 + c_3 C_f^3 \quad \text{Equation 2}$$

described in Revil et al. (A. Revil, P. A. Pezard, and P. W. J. Glover, "Streaming potential in porous media 1. Theory of the zeta potential," Journal of Geophysical Research B: Solid Earth, vol. 104, no. 9, pp. 20021-20031, 1999) and $\varepsilon f = \varepsilon_o * \varepsilon_r$, where $\varepsilon_o = 8.854 \times 10^{-12}$ F/m as described in Glover (P. W. J. Glover, E. Walker, and M. D. Jackson, "Streaming potential coefficient of reservoir rock: a theoretical model," Geophysics, vol. 77, no. 2, pp. D17-D43, 2012). The core testing system 100 operation maintains the first fluid 106 in the core holder 104 and prevents the first fluid 106 from exiting the upstream and downstream components 110a, 110b using the second fluid 108 as a buffer.

The second fluid 108 is less conductive than the first fluid 106. In some implementations, the second fluid 108 is non-conductive. The first fluid 106 serves as an electrical conductor and the second fluid 108 serves as an electrical insulator. The first fluid 106 and the second fluid are immiscible. In this implementation, the second fluid is mineral oil. Alternatively, the second fluid can be other types of non-conductive fluids. The mineral oil has a permittivity of between one and three. In this implementation, the average permittivity is two. The second fluid 108 is an electrically isolating buffer fluid in the core testing system 100. The conductivity of the second fluid should be close to or at zero. The viscosity of the second fluid should be close to or equal to the viscosity of water.

The first set 110a of components are referred to as upstream of the core holder 104 and the second set 110b of components are referred to as downstream of the core holder 104. Based on the configuration of the core testing system (described in more detail below), the first fluid 106 can flow either in a downstream direction 112 (i.e., from the upstream components 110a) or an upstream direction 114 (i.e., from the downstream components 110b) through the core holder 104. The upstream components 110a include an upstream reservoir 116a, an upstream trap 118a, an upstream external electrode cell 120a, and an upstream end piece 122a of the core holder 104. The downstream components 110b include a downstream reservoir 116b, a downstream trap 118b, a downstream external electrode cell 120b, and a downstream end piece 122b of the core holder 104 which are substantially similar to the upstream reservoir 116a, the upstream trap 118a, the upstream external electrode cell 120a, and the upstream end piece 122a, respectively. The upstream and downstream end pieces 122a, 122b are described in more detail in reference to FIG. 2. The upstream and downstream external electrode cells 120a, 120b are described in more detail in reference to FIG. 3.

The core holder 104 includes a sealed pressure vessel 124 with a first end 126 and a second end 128. The second end 128 is opposite the first end 126. The core holder 104 is sized to contain the core plug 102. The first end 126 and the second end 126 are removable so an operator can remove and replace the core plug 102 from the sealed pressure vessel 124. The first end 126 and the second end 126 are threadedly coupled to the sealed pressure vessel 124. The upstream end piece 122a is positioned at and extends through the first end 126. The downstream end piece 122b is positioned at and extends through the second end 126. The first fluid 106 flows between the first end 126 and the second end 128 to generate the streaming potential when the core plug 102 is contained within the core holder 104.

The core holder 104 includes a pressure gauge 130. The pressure gauge 130 senses pressure within the core holder 104. In some cases, the pressure within the core holder 104 is a confining pressure. The pressure gauge 130 has inlet and outlet transducers and the pressure difference is transmitted to the data acquisition system 158. The pressure drop across the core sample should not exceed the difference between the confining pressure and the back pressure. In some implementations, the maximum operating pressure of the core holder is 5,000 pounds per square inch.

The core testing system 100 includes fluid conduits 132a-j fluidly coupling the various components of the core testing system 100. The fluid conduits 132a-j conduct the first fluid 106 and the second fluid 108 between components. The fluid conduits 132a-Z include various fittings, hoses, and pipes. Other fluid conduits between some components are shown but not labeled.

The first end 126 of the core holder 104 is coupled to the upstream external electrode cell 120a by fluid conduit 132a. The second end 128 of the core holder is coupled to the downstream external electrode cell 120b by fluid conduit 132b.

Figure 2:
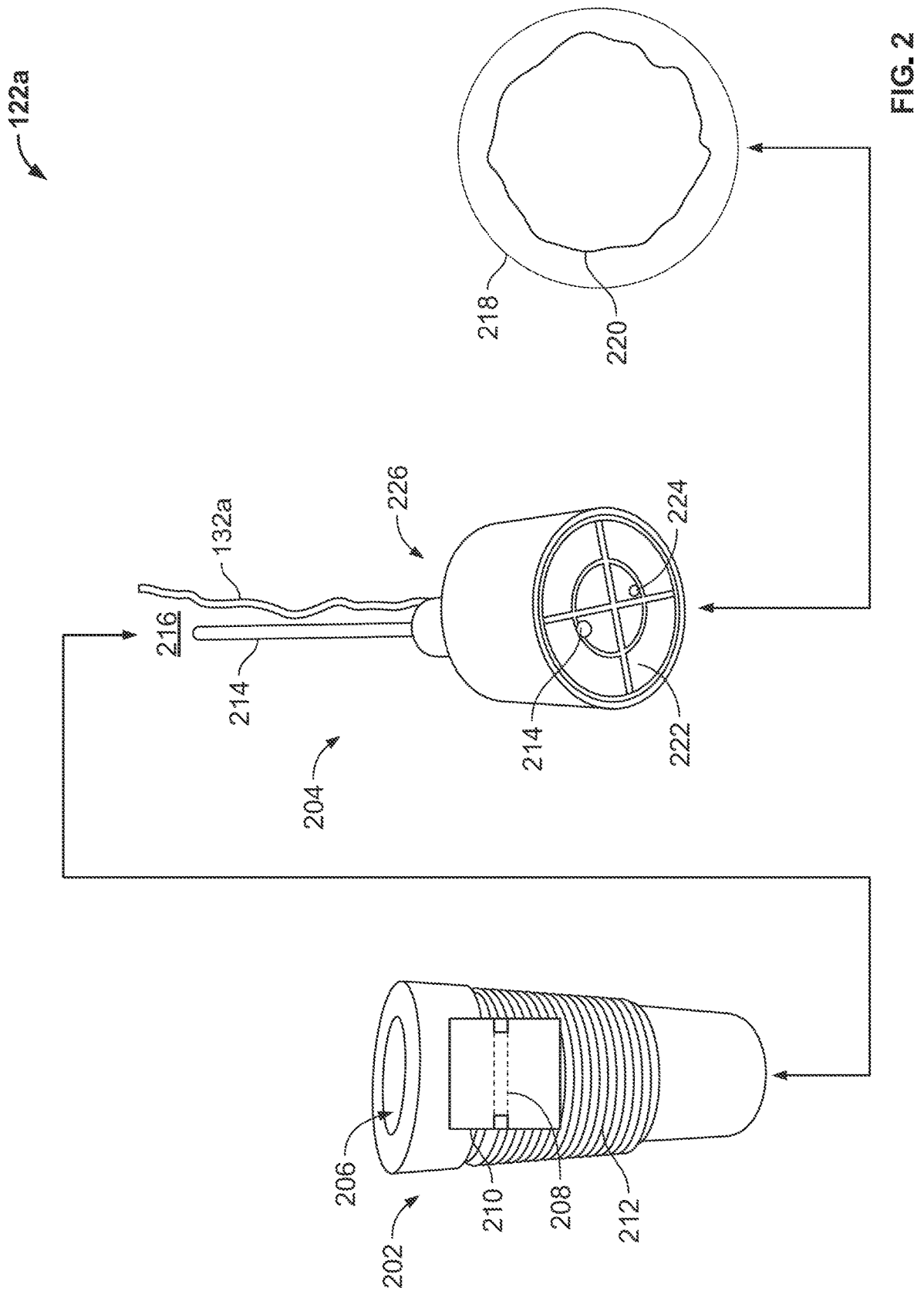
FIG. 2 is a schematic view of an end piece of a core holder of the core testing system of FIG. 1.

FIG. 2 is a schematic view of the upstream and downstream end pieces 122a, 122b of the core holder 104 of the core testing system 100 shown in FIG. 1. The upstream end piece 122a is shown in FIG. 2. The downstream end piece 122b is substantially similar to upstream end piece 122a. The upstream and downstream end pieces 122a, 122b seal the first and second ends 126, 128 of the core holder 104 and allow the first fluid 106 to pass into and out of the core holder 104. The end piece 122a is positioned at and extends through the first end 126 (as shown in FIG. 1). The upstream and downstream end pieces 122a, 122b include a cylindrical body 202 and a cap 204.

The cylindrical body 202 has a void 206 extending through the cylindrical body 202 and a rim 208 within the void 206, as seen in cutout 210. The void 206 is sized to receive and hold the cap 204 within the void 206 by contacting the rim 208. The cylindrical body 206 has external threads 212 to threadedly couple to the respective first or second ends 126, 126 of the core holder 104.

The cylindrical body 202 is manufactured from a non-conductive material. For example, the cylindrical body 202 can be made from polytetrafluoroethylene (PTFE) or polyether ether ketone (PEEK). These materials reduce electrical transmissions and noise into the core testing system 100.

The cap 204 includes an electrode 214. The electrode extends through the cap 204 from the void 206 to a space 216 outside the void 206. The electrode 214 is in electrical contact with the first fluid 106. A multimeter 132 (described in more detail later in reference to FIG. 1) can be coupled to upstream and downstream end pieces 122a, 122b by the respective electrode 214 to determine the streaming potential when the first fluid 106 is flowed through the core holder 104. The electrode 214 is connected to the multimeter 132 to measure the generated streaming potential. In this implementation, the electrodes 214 are exposed to brine flow while in the upstream and downstream external electrode cells 120a, 120b are less exposed to brine flow where relatively stable streaming potential is obtained. In some cases, the electrode 214 is a silver rod. The cap 204 is constructed from a non-conductive material such PTFE or PEEK.

The upstream and downstream end pieces 122a, 122b include a silver membrane filter 218 coupled to the electrode 214 by a conductive silver paste 220. The silver membrane filter 218 is positioned on an inner surface 222 of the cap 204. The silver membrane filter 218 is permeable and the first fluid 106 can flow through the silver membrane filter 218. The silver membrane filter 218 and silver paste 220 further reduce the electrical resistance of the upstream and downstream end pieces 122a, 122b, allowing lower magnitude voltages and lower magnitude changes in voltage to be detected by the multimeter 132. The silver membrane filter 218 can be between a two micron and a twenty micron filter. In some implementations, the silver membrane filter 218 is a five micron filter. In some implementations, the conductive silver paste 220 has a silver purity of at least 99%.

The cap 204 has a fluid port 224 extending through the cap 204. The fluid port 224 is fluidly coupled to the respective fluid conduit 132a (shown in FIG. 2) or fluid conduit 132b on an outer surface 226. The fluid port extends to the inner surface 222 of the cap. The fluid port 224 conducts the first fluid 106 into and out of the core holder 104.

Referring to FIG. 1, the upstream reservoir 116a and the downstream reservoir 116b have a first portion 134 filled with the first fluid 106 and a second portion 136 filled with the second fluid 108. The reservoirs 116a, 116b both contain some of the first fluid 106 and the second fluid 108. Since the first fluid 106 and the second fluid 108 are immiscible, an interface 138 between the two fluids 106, 108 is formed in the reservoirs 116a, 116b. As the first fluid 106 flows into and out of the core holder 104, the interface 138 move within the reservoirs 116a, 116b depending on the direction of flow.

The first fluid 106 flows into and out of the upstream reservoir 116a through the fluid conduit 132c to and from the core holder 104. The second fluid 108 flows into and out of the upstream reservoir 116a through the fluid conduit 132d.

The first fluid 106 flows into and out of the downstream reservoir 116b through the fluid conduit 132e to and from the core holder 104. The second fluid 108 flows into and out of the downstream reservoir 116b through the fluid conduit 132f.

The upstream reservoir 116a and the downstream reservoir 116b have a body 140. In some implementations, the upstream reservoir 116a and the downstream reservoir 116b have a two piece body. The bodies 140 are a non-conductive material such as PTFE or PEEK to further electrically isolate the core holder 104 by reducing electrical transmissions.

Figure 3:
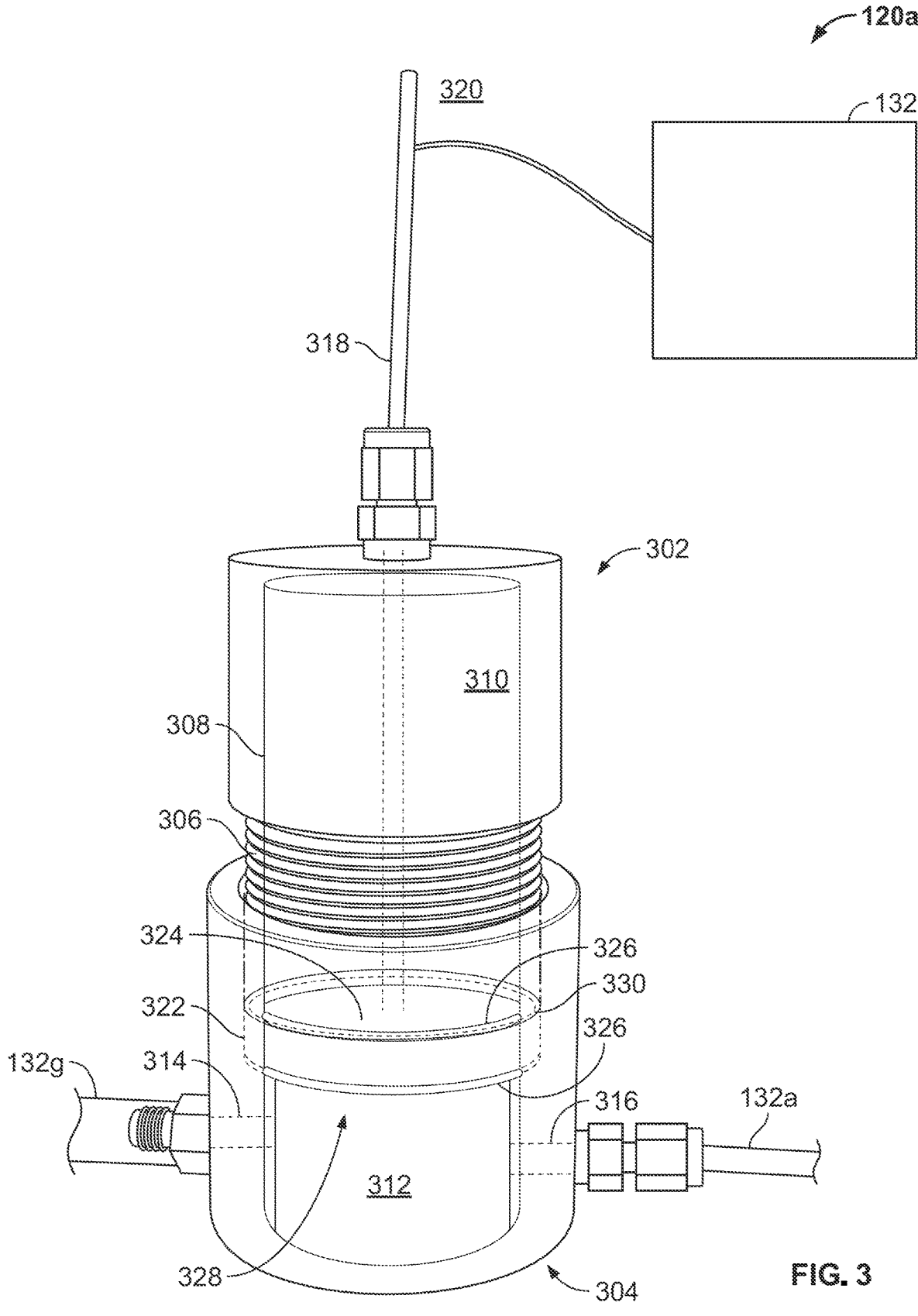
FIG. 3 is a schematic view of an external electrode cell of the core testing system of FIG. 1.

FIG. 3 is a schematic view of the upstream and downstream external electrode cells 120a, 120b of the core testing system 100 of FIG. 1. FIG. 3 is described in reference to the upstream external electrode cell 120a. The downstream external electrode cell 120b is substantially similar to the upstream external electrode cell 120a. Referring to FIGS. 1 and 3, the upstream and downstream external electrode cells 120a, 120b are electrically isolated from the core holder 104 and the other components of the core testing system 100 by the upstream and downstream components 110a, 110b and the second fluid 108, while still flowing the first fluid 106 though the core holder 104 to produce the streaming potential and the associated zeta potential. The multimeter 132 is electrically coupled to the upstream and downstream external electrode cells 120a, 120b to measure the streaming potential and zeta potential.

The upstream external electrode cell 120a has an upper body 302 and a lower body 304 coupled to the upper body 302. The upper body 302 is threaded into the lower body 304 by a threaded connection 306. The upstream external electrode cell 120a has a chamber 308, with the upper body 302 including an upper portion 310 of the chamber 308 and the lower body 304 including a lower portion 312 of the chamber 308. The chamber 308 is filled with the first fluid 106 in electrical contact with the core holder 104. The upper body 302 and the lower body 304 are made of a non-conductive material such as PTFE or PEEK to further electrically isolate the core holder 104 by reducing electrical transmissions.

The lower body 302 has a first port 314 fluidly coupled to the lower portion 312 of the chamber 308 and a second port 316 fluidly coupled to the chamber 308. The first fluid 106 is free to flow between the first port 314 and the second port 316 through the chamber 308. The first port 314 of the upstream external electrode cell 120a is fluidly coupled to the upstream reservoir 116a and the upstream trap 118a by a fluid conduit 132g through a first three-way splitter 142a. The first three-way splitter 142a is fluidly coupled to the upstream reservoir 116a by the fluid conduit 132c and the upstream trap 118a by the fluid conduit 132h. The first port 314 of the downstream external electrode cell 120b is fluidly coupled to the downstream reservoir 116b and the downstream trap 118b by the fluid conduit 132i through a second three-way splitter 142b. The second three-way splitter 142b is fluidly coupled to the downstream reservoir 116a by the fluid conduit 132e and the downstream trap 118b by the fluid conduit 132j.

The second port 316 of the upstream external electrode cell 120a is fluidly coupled to the upstream end piece 122a of the core holder 104 by the fluid conduit 132a. The second port 316 of the downstream external electrode cell 120b is fluidly coupled to the second end 128 of the core holder 104 by the fluid conduit 132b.

The upstream external electrode cell 120a has an electrode 318. The electrode 318 extends from the chamber 308 to a space 320 outside the chamber 308. The electrode 318 conducts the zeta potential outside the upstream external electrode cell 120*a* so the zeta potential can be measured. The multimeter 132 is electrically coupled to each of the respective electrodes 318 of the upstream external electrode cell 120*a* and the downstream external electrode cell 120*b* (as shown in FIG. 1) to measure the zeta potential. In this implementation, the electrodes 318 are silver rods.

The upstream external electrode cell 120*a* includes a ceramic disk 322 positioned between the upper portion 310 and the lower portion 312 of the chamber 308. The ceramic disk 322 has a homogenous permeability and provides a uniform flow of the first fluid 106 to the electrode 318. The ceramic disk 322 holds a silver membrane filter 324, generally similar to the silver membrane filter 218 previously described, in contact with the electrode 318. The lower body 304 and the upper body 302 fit together to hold the ceramic disk 322 in place. The ceramic disk 322 separates the upper portion 310 of the chamber 308 from the lower portion 312 of the chamber 308. The ceramic disk 322 has a porosity of between 20% and 40%. In this implementation, the ceramic disk 322 has a porosity of 30%. The ceramic disk 322 can have a pore size between 20-30 μm and a porosity of 40%.

The ceramic disk 322 has a thickness of between one and two millimeters. In this implementation, the thickness of the ceramic disk is one and a half millimeters. The ceramic disk has a diameter of between two and three millimeters. In this implementation, the diameter of the ceramic disk is two and a half millimeters. The diameter of the ceramic disc is equivalent to the core plug diameter.

The upstream external electrode cell 120*a* includes a first o-ring 326 sealing a bottom surface 328 of the ceramic disk and includes another o-ring 326 sealing a top surface 330 of the ceramic disk 322. The o-rings 326 prevent the first fluid 106 from flowing out of the upstream external electrode cell 120 past the threaded connection 306.

Referring to FIG. 1, the upstream trap 118*a* and the downstream trap 118*b* provide a buffer volume for the first fluid 106. For example, when the first fluid 106 flows from the upstream reservoir 116*a* in the downstream direction 112 through the core holder 104 and out the second end 128 of the core holder 104 past the downstream external electrode cell 120*b*, then out the downstream external electrode cell 120*b*, the first fluid 106 can then flow into the downstream trap 118*b*. Alternatively, when the first fluid 106 flows from the downstream reservoir 116*b* in the upstream direction 114 through the core holder 104 and out the first end 126 of the core holder 104 past the upstream external electrode cell 120*a*, then out the upstream external electrode cell 120*a*, the first fluid 106 can flow into the upstream trap 118*a*.

The upstream and downstream traps 118*a*, 118*b* have a body 144. The body 144 is a non-conductive material. For example, the body 144 can be PEEK or PTFE.

The core testing system 100 includes a second fluid supply system 146 to selectively flow the second fluid 108 to the upstream and downstream reservoirs 116*a*, 116*b*, forcing the first fluid 106 to flow in either the downstream direction 112 or the upstream direction 114 generating the streaming potential. The second fluid supply system 146 includes a second fluid reservoir 148, a back pressure regulator 150, a first actuated valve 152, an injection pump 154, a second actuated valve 156, a third three-way splitter 142*c*, and a fourth three-way splitter 142*d*.

The back pressure regulator 150 maintains the pressure of the core testing system 100. The back pressure regulator 150 regulates the pressure of the opposite side above a threshold pressure from the side being used (i.e., either the upstream or downstream section) during operation of the injection pump 154 flowing the second fluid 108 to either the upstream reservoir 116*a* through the first actuated valve 152 or the downstream reservoir 116*b* through the second actuated valve 156.

The first actuated valve 152 and the second actuated valve 156 are operable between open positions and closed positions. When in the open position, second fluid 108 flow through the respective actuated valve 152, 156 is allowed. When in the closed position, second fluid 108 flow through the respective actuated valve 152, 156 is prevented.

The first actuated valve 152 is positioned between the injection pump 154 and the upstream reservoir 116*a*. The second actuated valve 156 is positioned between the injection pump 154 and the downstream reservoir 116*b*.

When the first actuated valve 152 is in the open position, the second actuated valve 156 is in the closed position, and the injection pump 154 is running, the second fluid 108 flows from the second fluid reservoir 148, is pressurized by the injection pump 154, exits the injection pump 154, flows through the fourth three-way splitter 142*d* to both the first actuated valve 152 and the second actuated valve 156. The second fluid 108 flows through the second actuated valve 156 is prevented. The second fluid 108 flows through the first actuated valve 152 to the upstream reservoir 116*a*, forcing more second fluid 108 into the upstream reservoir 116*a*. This causes some of the first fluid 106 to flow out of the upstream reservoir 116*a*, through the upstream external electrode cell 120*a*, through the first end 126 of the core holder 104 and through the core plug 102, generating the steaming potential and the zeta potential. The first fluid 106 flows out the core holder 104 to the downstream external electrode cell 120*b* and into the downstream trap 118*b*.

When the first actuated valve 152 is in the closed position, the second actuated valve 156 is in the open position, and the injection pump 154 is running, the second fluid 108 flows from the second fluid reservoir 148, is pressurized by the injection pump 154, exits the injection pump 154, flows through the fourth three-way splitter 142*d* to both the first actuated valve 152 and the second actuated valve 156. The second fluid 108 flows through the first actuated valve 152 is prevented. The second fluid 108 flows through the second actuated valve 156 to the downstream reservoir 116*b*, forcing more second fluid 108 into the downstream reservoir 116*b*. This causes some of the first fluid 106 to flow out of the downstream reservoir 116*b*, through the downstream external electrode cell 120*b*, through the second end 128 of the core holder 104 and through the core plug 102, generating the steaming potential and the zeta potential. The first fluid 106 flows out the core holder 104 to the upstream external electrode cell 120*a* and into the upstream trap 118*a*. This is a reverse flow configuration.

The core testing system 100 includes a data acquisition system 158 coupled to the core holder 104. The data acquisition system 158 measures a differential pressure across the core holder 104. The differential pressure across the core holder 104 (i.e., the differential pressure of the core plug 102) is used to determine the zeta potential of the core plug. The data acquisition system 158 is positioned between the first end 126 and the second end 128 of the core holder 104. Specifically, the data acquisition system 158 is fluidly coupled to the upstream trap 118*a* and the downstream trap 118*b*.

The core testing system 100 includes a controller 160 to operate the second fluid supply system 146 and determine the zeta potential from the streaming potential and the differential pressure of the core plug 102. The controller 160 receives the streaming potential (i.e., the voltage across the core holder 104) from the multimeter 132 and the differential pressure across the core holder 104 from the data acquisition system 158.

The controller 160 can be a computer and a microprocessor. The controller 160 has one or more sets of programmed instructions stored in a memory or other non-transitory computer-readable media that stores data (e.g., connected with the printed circuit board), which can be accessed and processed by a microprocessor. The programmed instructions can include, for example, instructions for sending or receiving signals and commands to operate the second fluid supply system 146, determine the zeta potential from the streaming potential and the differential pressure of the core plug 102, and/or to collect and store data from the multimeter 132 and the data acquisition system 158. The controller 160 stores values (signals and commands) against which sensed values (signals and commands) representing the conditions can be compared.

Specifically, the controller 160 determines the zeta potential by the Helmholtz-Smoluchowski equation given below from the obtained streaming potential and the differential pressure by Equation 1 shown below.

$$\nabla V / \nabla P = (\varepsilon \zeta)/(4\pi\eta\lambda) \qquad \text{Equation 1:}$$

In Equation 1, $\varepsilon$ is the dielectric constant of the first fluid 106. $\zeta$ is the zeta potential to be determined. $\nabla P$ is the differential pressure across the core holder 104. $\eta$ is the viscosity of the first fluid 106. $\lambda$ is the specific conductivity of the first fluid 106. The ratio $\nabla V / \nabla P$ is the streaming potential coupling coefficient.

Table 1 illustrates a determination of the streaming potential coupling coefficient for Indiana Limestone using two systems, one from Luong and Sprik (Luong, D. T. and Sprik, R. Examination of a Theoretical Model of Streaming Potential Coupling Coefficient. International Journal of Geophysics Volume 2014, Article ID 471819, 12 pages http://dx-.doi.org/10.1155/2014/471819) and the other from the core testing system 100.

the first fluid. The first fluid and the second fluid are immiscible. The core testing system includes a core holder having a first end and a second end. The core holder holds a core plug. The core testing system includes an upstream reservoir fluidly coupled to the first end of the core holder and a downstream reservoir fluidly coupled to the second end of the core holder. The core testing system includes an upstream trap fluidly coupled to the first end of the core holder and a downstream trap fluidly coupled to the second end of the core holder. The core testing system includes an upstream external electrode cell having a first port and a second port. The first port of the upstream external electrode cell is fluidly coupled to the upstream reservoir and the upstream trap. The second port of the upstream external electrode cell is fluidly coupled to the first end of the core holder. The core testing system includes a downstream external electrode cell having a first port and a second port. The first port of the downstream external electrode cell is fluidly coupled to the downstream reservoir and the downstream trap. The second port of the downstream external electrode cell is fluidly coupled to the second end of the core holder. The core testing system includes a multimeter electrically coupled to the upstream external electrode cell and the downstream external electrode cell. The core testing system includes a data acquisition system fluidly coupled between the first end and the second end of the core holder. The data acquisition system measures a differential pressure across the core holder. The core testing system includes a controller. The controller receives a signal representing the differential pressure across the core holder from the data acquisition system; receives a signal representing a voltage across the core holder from the multimeter; and based on the differential pressure and the voltage, determines a zeta potential of the core plug. Each of the upstream reservoir, the downstream reservoir, the upstream trap, and the downstream trap contain some of the second fluid. The first fluid fills the core holder and separates the second fluid from the core holder.

TABLE 1

|  | Rock Type | Permeability, md | 5 mM | 10 mM | 20 mM | 50 mM |
|---|---|---|---|---|---|---|
| Luong and Sprik | Indiana limestone | 103 | −13.5 | −7.6 | −3.7 | −1.8 |
| Core Testing System 100 | Indiana limestone | 206 | −13.21 | −7.34 | −3.75 | −1.86 |

Table 1 shows a decrease in the streaming potential coupling coefficient for the 5 mM, 10 mM, and 20 mM solutions, resulting in a corresponding increase in the zeta potential.

Figure 4:
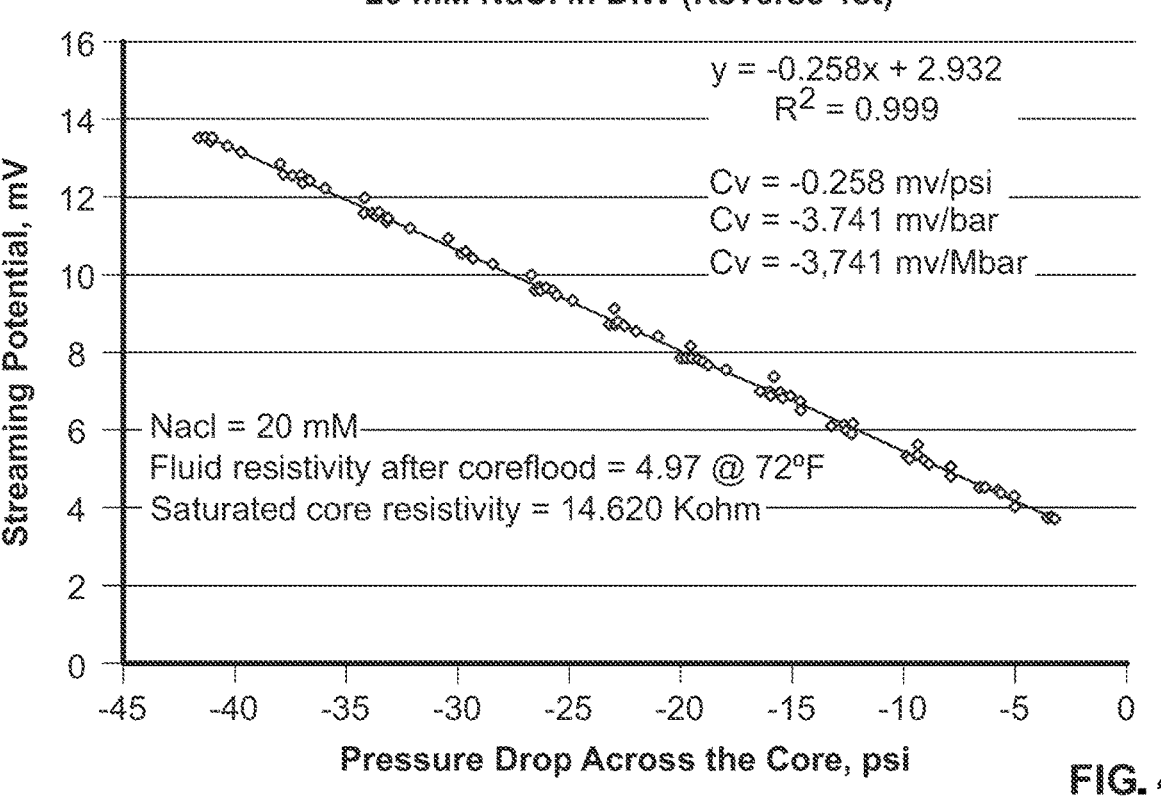
FIG. 4 is a graph of streaming potential relative to pressure drop across a core sample for Indiana limestone (Reverse $1^{st}$ Run).
Figure 5:
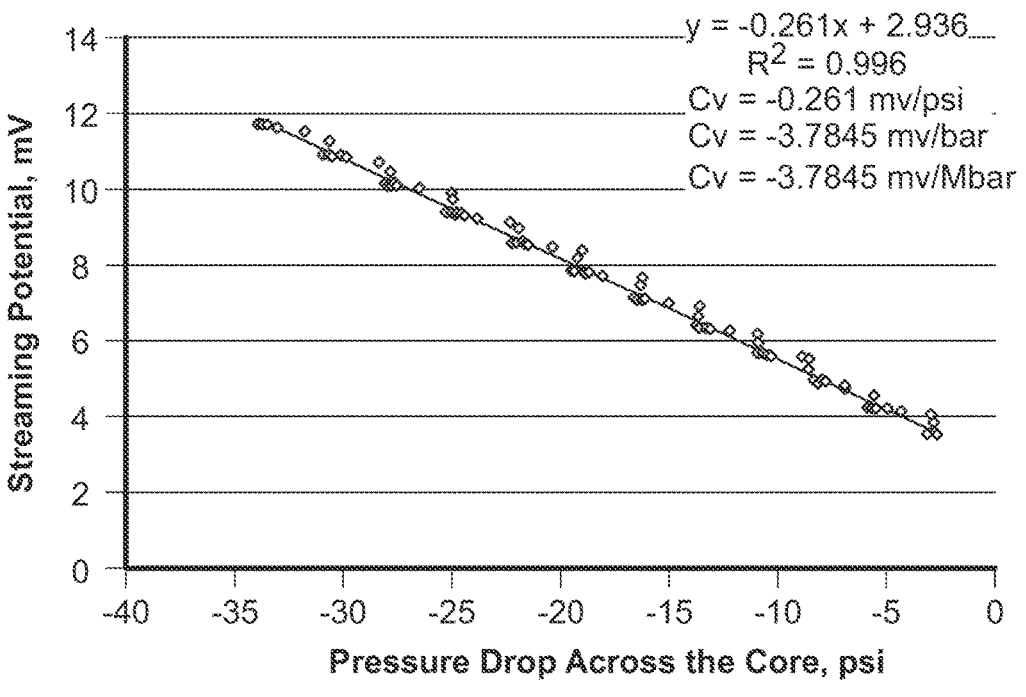
FIG. 5 is a graph of streaming potential relative to pressure drop across a core sample for Indiana limestone (Reverse $3^{rd}$ Run).
Figure 6:
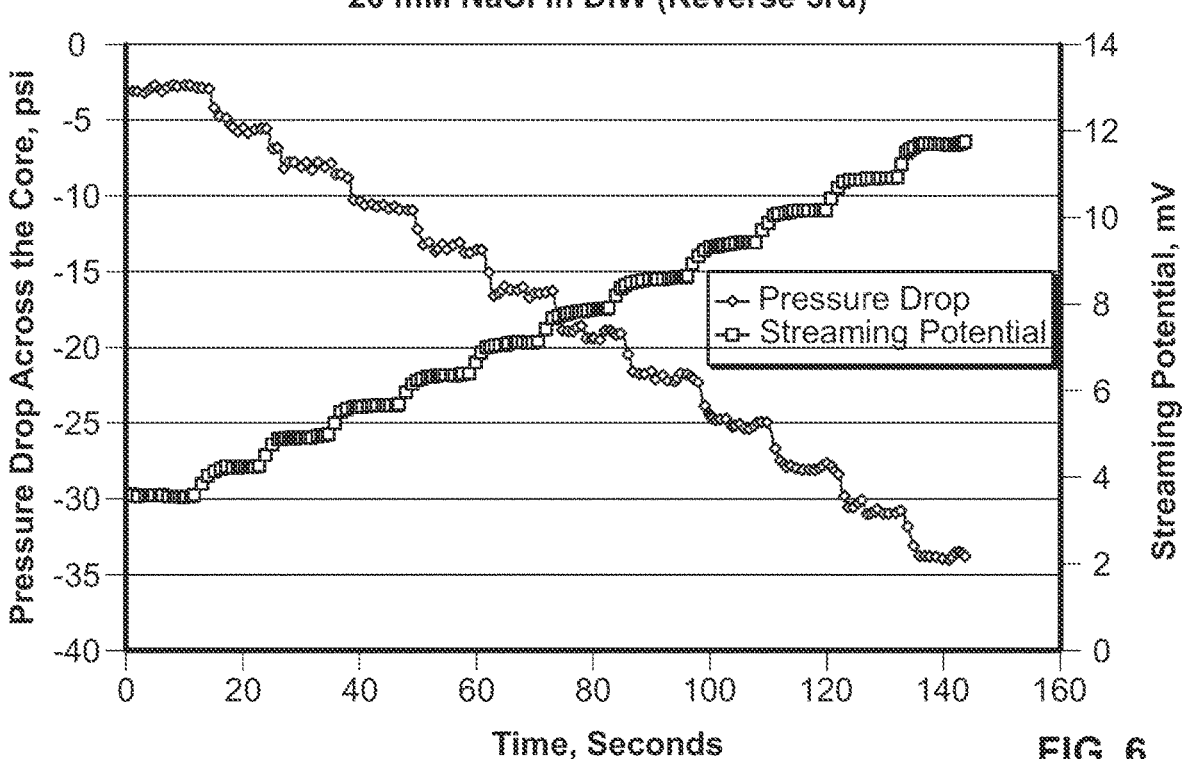
FIG. 6 is a graph of streaming potential and pressure drop relative to time across a core sample for Indiana limestone (Reverse $3^{rd}$ Run).

FIG. 4 is a graph of streaming potential relative to pressure drop across a core sample for Indiana limestone (Reverse 1ˢᵗ). FIG. 5 is a graph of streaming potential relative to pressure drop across a core sample for Indiana limestone (Reverse 3ʳᵈ Run). FIG. 6 is a graph of streaming potential and pressure drop relative to time across a core sample for Indiana limestone (Reverse 3ʳᵈ Run). The first run was performed on the production side. Three runs were performed, and the average of the runs was considered. The streaming potential coupling coefficient was determined based on the average of the runs.

EMBODIMENTS

In an example aspect, a core testing system includes a first fluid a second fluid. The second fluid is less conductive than In an example aspect combinable with any other example aspect, the first fluid includes brine and the second fluid includes mineral oil.

In an example aspect combinable with any other example aspect, the upstream reservoir, the upstream trap, the upstream external electrode cell, the downstream reservoir, the downstream trap, and the downstream external electrode cell each include a non-conductive material.

In an example aspect combinable with any other example aspect, each of the upstream external electrode cell and the downstream external electrode cell have a chamber and an electrode. The chamber fluidly couples the first port to the second port. The electrode extends from the chamber to a space outside the chamber. The multimeter is electrically coupled to each of the respective electrodes of the upstream external electrode cell and the downstream external electrode cell.

In an example aspect combinable with any other example aspect, the first fluid is free to flow between the first port and the second port through the chamber.

In an example aspect combinable with any other example aspect, each of the upstream external electrode cell and the downstream external electrode cell have a lower body and an upper body. The lower body includes the first port, the second port, and a first portion of the chamber. The upper body is threadedly coupled to the lower body. The upper body includes a second portion of the chamber. The electrode extends through the upper body to the second portion of the chamber.

In an example aspect combinable with any other example aspect, each of the upstream external electrode cell and the downstream external electrode cell have a ceramic disk positioned in the chamber between the electrode and the first and second ports.

In an example aspect combinable with any other example aspect, the lower body and the upper body hold the ceramic disk in the chamber between the first portion and the second portion of the chamber.

In an example aspect combinable with any other example aspect, a porosity of the ceramic disk is between 20% and 40%.

In an example aspect combinable with any other example aspect, the electrode includes a silver rod.

In an example aspect combinable with any other example aspect, the core testing system includes a first end piece and a second end piece. The first end piece and the second end piece seal the first end and the second end of the core holder, respectively. The first and second end pieces each have a cylindrical body and cap. The cylindrical body has external threads. The cylindrical body has a void and a rim positioned within the void. The cap is positioned within the void and retained within the void by the rim.

In an example aspect combinable with any other example aspect, the first end piece and the second end piece each have an electrode extending through the cap from the void to a space outside the void.

In an example aspect combinable with any other example aspect, the core testing system includes a silver membrane filter coupled to the electrode by a conductive silver paste.

In an example aspect combinable with any other example aspect, the first end piece and the second end piece each include a fluid port fluidly coupled to the respective upstream external electrode cell and the downstream external electrode cell.

In an example aspect combinable with any other example aspect, the core testing system includes a pressure gauge coupled to the core holder.

In an example aspect combinable with any other example aspect, the core testing system includes a first splitter and a second splitter. The first splitter has a first fluid port coupled to the upstream external electrode cell, a second fluid port coupled to the upstream trap, and a third fluid port coupled to the upstream reservoir. The second splitter has a first fluid port coupled to the downstream external electrode cell, a second fluid port coupled to the downstream trap, and a third fluid port coupled to the downstream reservoir.

In an example aspect combinable with any other example aspect, the core testing system includes a second fluid supply system having a second fluid reservoir, a back pressure regulator, a first actuated valve, an injection pump, a second actuated valve, a third splitter, and a fourth splitter. The back pressure regulator is fluidly coupled to the second fluid reservoir. The first actuated valve is fluidly coupled to the upstream reservoir. The injection pump is fluidly coupled to the second fluid reservoir. The second actuated valve is fluidly coupled to the downstream reservoir. The third splitter is fluidly coupled to the back pressure regulator, the second actuated valve, and the first actuated valve. The fourth splitter is fluidly coupled to the second actuated valve, the first actuated valve, and the injection pump.

In an example aspect combinable with any other example aspect, based on an open condition of the first actuated valve and a closed condition the second actuated valve, the second fluid supply system flows the second fluid to force the first fluid from the upstream reservoir through the upstream external electrode cell to the first end of the core holder, and through the core holder.

In an example aspect combinable with any other example aspect, based on a closed condition of the first actuated valve and an open condition of the second actuated valve, the second fluid supply system flows the second fluid to force the first fluid from the downstream reservoir through the downstream external electrode cell to the second end of the core holder, and through the core holder.

In another example aspect, an external electrode cell has a lower body, an upper body, a ceramic disk, and an electrode. The lower body has a first portion of a chamber, a first port fluidly coupled to the first portion of the chamber, and a second port fluidly coupled to the first portion of the chamber. The upper body is threadedly coupled to the lower body. The upper body includes a second portion of the chamber. The ceramic disk is positioned between the lower body and the upper body. The ceramic disk separates the first portion of the chamber from the second portion of the chamber. The electrode extending from the second portion of the chamber through the upper body.

Although the present implementations have been described in detail, it should be understood that various changes, substitutions, and alterations can be made hereupon without departing from the principle and scope of the disclosure. Accordingly, the scope of the present disclosure should be determined by the following claims and their appropriate legal equivalents.

The invention claimed is:

1. A core testing system comprising:
a first fluid;
a second fluid that is less conductive than the first fluid, wherein the first fluid and the second fluid are immiscible;
a core holder comprising a first end and a second end, the core holder configured to hold a core plug;
an upstream reservoir fluidly coupled to the first end of the core holder and a downstream reservoir fluidly coupled to the second end of the core holder;
an upstream trap fluidly coupled to the first end of the core holder and a downstream trap fluidly coupled to the second end of the core holder;
an upstream external electrode cell comprising a first port and a second port, the first port of the upstream external electrode cell fluidly coupled to the upstream reservoir and the upstream trap, and the second port of the upstream external electrode cell fluidly coupled to the first end of the core holder;
a downstream external electrode cell comprising a first port and a second port, the first port of the downstream external electrode cell fluidly coupled to the downstream reservoir and the downstream trap, and the second port of the downstream external electrode cell fluidly coupled to the second end of the core holder;

a multimeter electrically coupled to the upstream external electrode cell and the downstream external electrode cell;

a data acquisition system fluidly coupled between the first end and the second end of the core holder, the data acquisition system configured to measure a differential pressure across the core holder;

a controller configured to perform operations comprising:

receiving a signal representing the differential pressure across the core holder from the data acquisition system;

receiving a signal representing a voltage across the core holder from the multimeter; and based on the differential pressure and the voltage, determining a zeta potential of the core plug;

wherein each of the upstream reservoir, the downstream reservoir, the upstream trap, and the downstream trap contain some of the second fluid; and wherein the first fluid fills the core holder and separates the second fluid from the core holder.

2. The core testing system of claim 1, wherein the first fluid comprises a brine and the second fluid comprises a mineral oil.

3. The core testing system of claim 1, wherein the upstream reservoir, the upstream trap, the upstream external electrode cell, the downstream reservoir, the downstream trap, and the downstream external electrode cell each comprise a non-conductive material.

4. The core testing system of claim 1, wherein each of the upstream external electrode cell and the downstream external electrode cell comprise:

a chamber fluidly coupling the first port to the second port; and an electrode extending from the chamber to a space outside the chamber, the multimeter electrically coupled to each of the respective electrodes of the upstream external electrode cell and the downstream external electrode cell.

5. The core testing system of claim 4, wherein the first fluid is free to flow between the first port and the second port through the chamber.

6. The core testing system of claim 4, wherein each of the upstream external electrode cell and the downstream external electrode cell comprise:

a lower body comprising the first port, the second port, and a first portion of the chamber; and an upper body threadedly coupled to the lower body, the upper body comprising a second portion of the chamber, the electrode extending through the upper body to the second portion of the chamber.

7. The core testing system of claim 6, wherein each of the upstream external electrode cell and the downstream external electrode cell comprise a ceramic disk positioned in the chamber between the electrode and the first and second ports.

8. The core testing system of claim 7, wherein the lower body and the upper body hold the ceramic disk in the chamber between the first portion and the second portion of the chamber.

9. The core testing system of claim 7, wherein a porosity of the ceramic disk is between 20% and 40%.

10. The core testing system of claim 4, wherein the electrode comprises a silver rod.

11. The core testing system of claim 1, further comprising a first end piece and a second end piece, the first end piece and the second end piece sealing the first end and the second end of the core holder, respectively, the first and second end pieces comprising:

a cylindrical body comprising external threads, the cylindrical body comprising:

a void; and a rim positioned within the void; and a cap positioned within the void and retained within the void by the rim.

12. The core testing system of claim 11, wherein the first end piece and the second end piece each comprise an electrode extending through the cap from the void to a space outside the void.

13. The core testing system of claim 12, further comprising silver membrane filter coupled to the electrode by a conductive silver paste.

14. The core testing system of claim 11, wherein the first end piece and the second end piece each comprise a fluid port fluidly coupled to the respective upstream external electrode cell and the downstream external electrode cell.

15. The core testing system of claim 11, further comprising a pressure gauge coupled to the core holder.

16. The core testing system of claim 1, further comprising:

a first splitter comprising a first fluid port coupled to the upstream external electrode cell, a second fluid port coupled to the upstream trap, and a third fluid port coupled to the upstream reservoir; and a second splitter comprising a first fluid port coupled to the downstream external electrode cell, a second fluid port coupled to the downstream trap, and a third fluid port coupled to the downstream reservoir.

17. The core testing system of claim 15, further comprising a second fluid supply system comprising:

a second fluid reservoir;

a back pressure regulator fluidly coupled to the second fluid reservoir;

a first actuated valve fluidly coupled to the upstream reservoir;

an injection pump fluidly coupled to the second fluid reservoir;

a second actuated valve fluidly coupled to the downstream reservoir;

a third splitter fluidly coupled to the back pressure regulator, the second actuated valve, and the first actuated valve; and a fourth splitter fluidly coupled to the second actuated valve, the first actuated valve, and the injection pump.

18. The core testing system of claim 17, wherein based on an open condition of the first actuated valve and a closed condition the second actuated valve, the second fluid supply system flows the second fluid to force the first fluid from the upstream reservoir through the upstream external electrode cell to the first end of the core holder, and through the core holder.

19. The core testing system of claim 18, wherein based on a closed condition of the first actuated valve and an open condition of the second actuated valve, the second fluid supply system flows the second fluid to force the first fluid from the downstream reservoir through the downstream external electrode cell to the second end of the core holder, and through the core holder.

20. An external electrode cell comprising:

a lower body comprising:

a first portion of a chamber;

a first port fluidly coupled to the first portion of the chamber; and a second port fluidly coupled to the first portion of the chamber;

an upper body threadedly coupled to the lower body, the upper body comprising a second portion of the chamber;

a porous ceramic disk positioned between the lower body and the upper body, the porous ceramic disk positioned within the chamber and separating the first portion of the chamber from the second portion of the chamber;

an electrically conductive membrane filter positioned on the porous ceramic disk; and an electrode extending from the second portion of the chamber through the upper body to contact the electrically conductive membrane filter.

\* \* \* \* \*